(12) United States Patent
Andrews

(10) Patent No.: US 11,058,866 B2
(45) Date of Patent: Jul. 13, 2021

(54) GRAPHICALLY RESPONSIVE DEFIBRILLATION ELECTRODE PADS

(71) Applicant: Avive Solutions, Inc., San Francisco, CA (US)

(72) Inventor: Gordon Moseley P. Andrews, Ross, CA (US)

(73) Assignee: Avive Solutions, Inc., San Francisco, CA (US)

(*) Notice: Subject to any disclaimer, the term of this patent is extended or adjusted under 35 U.S.C. 154(b) by 116 days.

(21) Appl. No.: 16/580,887

(22) Filed: Sep. 24, 2019

(65) Prior Publication Data

US 2020/0094038 A1 Mar. 26, 2020

Related U.S. Application Data

(60) Provisional application No. 62/736,007, filed on Sep. 25, 2018.

(51) Int. Cl.
*A61N 1/04* (2006.01)
*A61N 1/39* (2006.01)
*G02F 1/157* (2006.01)

(52) U.S. Cl.
CPC ......... *A61N 1/046* (2013.01); *A61N 1/39044* (2017.08); *G02F 1/157* (2013.01)

(58) Field of Classification Search
CPC .. A61N 1/046; A61N 1/39044; A61N 1/0492; G02F 1/157
See application file for complete search history.

(56) References Cited

U.S. PATENT DOCUMENTS

| | | | | |
|---|---|---|---|---|
| 5,135,479 A | * | 8/1992 | Sibalis | A61M 37/00 604/20 |
| 2005/0277991 A1 | * | 12/2005 | Covey | A61N 1/0492 607/5 |
| 2007/0002007 A1 | * | 1/2007 | Tam | G09G 3/38 345/105 |
| 2012/0148797 A1 | * | 6/2012 | Tsai | B32B 5/12 428/137 |
| 2012/0176663 A1 | * | 7/2012 | Zang | G02F 1/1341 359/296 |
| 2016/0082246 A1 | * | 3/2016 | Piazza | A61N 1/0408 607/5 |
| 2017/0056650 A1 | * | 3/2017 | Cohen | A61N 1/3603 |
| 2018/0042508 A1 | * | 2/2018 | Lane | A61B 5/259 |
| 2018/0133507 A1 | * | 5/2018 | Malchano | A61B 5/38 |

* cited by examiner

*Primary Examiner* — Mallika D Fairchild
(74) *Attorney, Agent, or Firm* — Beyer Law Group LLP

(57) ABSTRACT

A variety of graphically responsive defibrillation electrode pads are described that can selectively display different images during use. The graphically responsive pads include a base electrode pad structure, at least two graphics, and one or more controllable layers that have multiple states. In some embodiments, the controllable layer incorporates an electrochromic material. In a first (opaque) state, the controllable layer hides the first graphic such that only the second graphic is visible to a user on the back side of the defibrillation electrode pad. When the controllable layer transitions to a second (transparent) state, the first graphic is made visible to thereby cause a composite image that combines the first and second graphics to be visible on the back side of the pad. In some embodiments, the electrochromic layer defaults to the opaque state when no power is applied to the electrochromic layer.

17 Claims, 8 Drawing Sheets

GRAPHICALLY RESPONSIVE DEFIBRILLATION ELECTRODE PADS

CROSS REFERENCE TO RELATED APPLICATIONS

The present application claims the priority of U.S. Provisional Patent Application No. 62/736,007 filed Sep. 25, 2018, which is incorporated herein by reference in its entirety.

FIELD

The present disclosure relates generally to defibrillation electrode pads. More particularly defibrillation electrode pads capable of changing graphics displayed thereon during use, and defibrillators suitable for controlling the graphics displayed on such electrode pads are described.

BACKGROUND

Automated external defibrillators (AEDs) are portable devices designed to be used by lay responders to treat victims of sudden cardiac arrest. The AED automatically checks for life-threatening heart rhythms associated with sudden cardiac arrest and when appropriate, sends an electrical shock to the heart to try to restore a normal rhythm when a shockable heart rhythm is detected. Most AEDs include a pair of disposable electrode pads that are electrically connected to the defibrillator by conductive wires. The electrode pads are typically quite flexible and thin and are designed to adhere to a patient's chest to facilitate use of the defibrillator.

FIGS. 1 and 2 respectively are back and cross sectional views of a representative defibrillator electrode pad 300. Although the geometry and construction of conventional defibrillator electrodes pads vary, most such pads include a number of layers. Some of the most common layers are illustrated in FIG. 2. These include a back layer 320, a conductor layer 330, a conductive gel layer 350 and a removable release carrier sheet 360 which is sometimes referred to as a release layer. The back layer 320 is typically formed from an insulating material such as a thin polyester plastic layer or an insulting foam material. Conductor layer 330 is adhered to the top surface of the back layer 320. Often the conductor 330 is a thin metal foil such as tin. However a variety of other structures are sometimes used, as for example a carbon filled polymer with a thin metal coating plated thereon. A conductive gel layer 350 is applied to conductor layer 330. The release layer 360 is adhered to the gel layer 350. The release layer 360 protects the conductive gel layer during storage of the electrode pads and helps prevent the gel from drying out and hardening during storage. To use the electrode pads, the release layers are peeled from the remainder of the electrodes (or vice versa) to expose conductive gel 350 and the pad is applied to the patient's skin. The gel helps make good electrical contact between the electrodes and the patient's skin.

Often, graphics 322 will be printed on the back side of back layer 320. The graphics often include an image and/or text that provide some level of instructions regarding pad placement. For example, graphic 322 may include an image of a person showing the desired pad placement for an adult patient. Although conventional AED electrode pads work well, there are continuing efforts to provide improved defibrillation electrode pads that may be easier to use during emergency cardiac incidents.

SUMMARY

A variety of graphically responsive defibrillation electrode pads are described that can selectively display different images during use.

In some embodiments, the graphically responsive pads include a base electrode pad structure that may be similar in structure to any conventional defibrillation pad. The defibrillation pad further includes first and second graphics and a controllable layer. The controllable layer has multiple states. In a first (opaque) state, the controllable layer hides the first graphic such that only the second image is visible to a user on the back side of the defibrillation electrode pad. When the controllable layer transitions to a second (transparent) state, the first graphic is made visible to thereby cause a composite image that combines the first and second graphics to be visible on the back side of the pad. In some embodiments, the controllable layer is an electrochromic layer that includes an electrochromic material. In some embodiments, the electrochromic layer defaults to the opaque state when no power is applied to the electrochromic layer.

In some embodiments the first graphic is printed on an insulating layer of the base electrode pad structure. In other embodiments, the first graphic is part of a first graphic layer positioned between the insulting layer and the electrochromic layer. Similarly, in some embodiments the second graphic is printed on the electrochromic layer. In other embodiments, the second graphic is part of a second graphic layer positioned on an opposite side of the electrochromic layer as the first graphic layer.

In some embodiments, the electrochromic layer is substantially opaque in the first state and substantially transparent in the second state. The transparent state may be clear or colored. In some embodiments, the electrochromic layer defaults to the opaque state when no power is applied thereto.

In some embodiments, one or more additional controllable layers and corresponding additional graphics may be provided. For example, a second electrochromic layer and a third graphic may be provided to facilitate more display options. In some embodiments, the second electrochromic layer is configured to hide the third graphic when the second electrochromic layer is in an opaque state and to render the third graphic visible when the second electrochromic layer is in a transparent state and the first graphic is visible to thereby cause a composite image that combines the first, second and third graphics to be visible on the back side of the defibrillation electrode pad.

In some embodiments, the defibrillation electrode pad further includes a cable. The cable may include a defibrillation lead and one or more control leads.

The described defibrillation electrode pads may be integrated into a defibrillator pad assembly includes a pair of the pads, a pair of cables, and a connector suitable for electrically connecting the defibrillator pad assembly to a defibrillator.

Defibrillators designed to work with the described pad assemblies include a defibrillator controller configured to control the images displayed by the defibrillation electrode pads during emergency use of the defibrillator system.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

AEDs typically provide audio user instructions during emergency use of the defibrillator. Some AEDs also display various graphics on a display screen that compliment the audio instructions. Although such audio and graphic instructions work well, it can be beneficial to compliment such conventional instructions with information presented on the electrode pads themselves. For example, as discussed in the background, conventional defibrillation electrode pads often have a graphic image printed on the back surface of the electrode that shows the proper pad placement. However, current defibrillation electrode pads are limited by only having a static graphic on the back surface of the electrode. The graphic cannot change even as the medical situation in which it is being used may be changing. We believe that advantages can be realized by providing defibrillation pads that can display different graphics during emergency use.

For example, there are times during use of an AED when responders may be instructed not to touch the patient. This includes both: (a) when the shock is being delivered (so that the rescuer(s) doesn't/don't get shocked); and (b) for most AEDs when the AED is analyzing the patient's heart rhythm. The later is particularly important when the user is performing CPR since CPR may interfere with the ability of some defibrillators to properly analyze the patient's heart rhythms Since a responder performing CPR is likely focusing on the chest compressions, it would be helpful to graphically display certain instructions or warnings at a location within the responder's field of view (the patient's chest) while they are performing CPR so they don't need to stop performing CPR to check the defibrillator to see the instructions. Such messages may include instructions such as "do not touch the patient" and/or images that convey a similar message.

In some embodiments, the active graphic interface is achieved by adding one or more electrochromic (EC) layers to the back surface of a base defibrillation electrode pad, along with graphics between each EC layer, and at either end of a series of EC layers. EC materials are materials that change in color or opacity when subjected to an electric field. For instance an EC material may have an opaque state when no voltage is applied and change to a transparent (clear) state when a designated voltage is applied.

Figure 1:
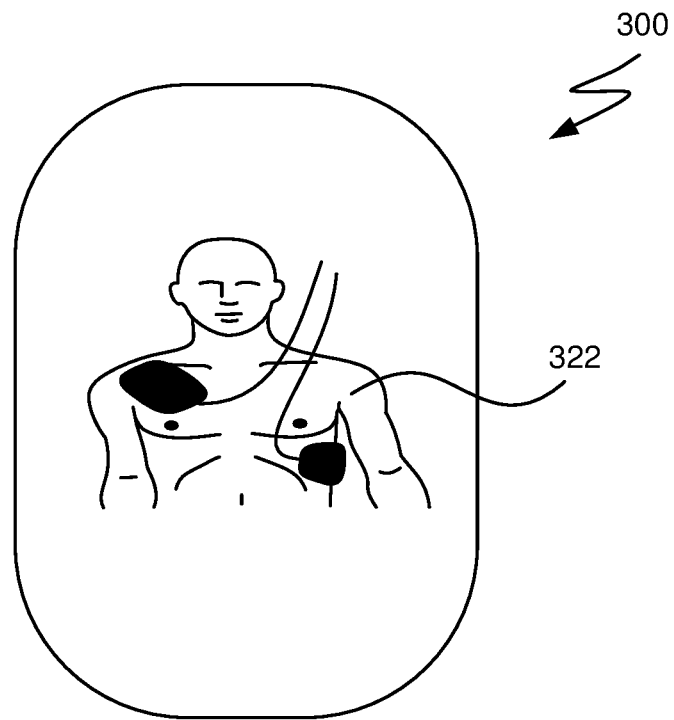
FIG. 1 is a back view of a conventional defibrillator electrode pad.
Figure 2:
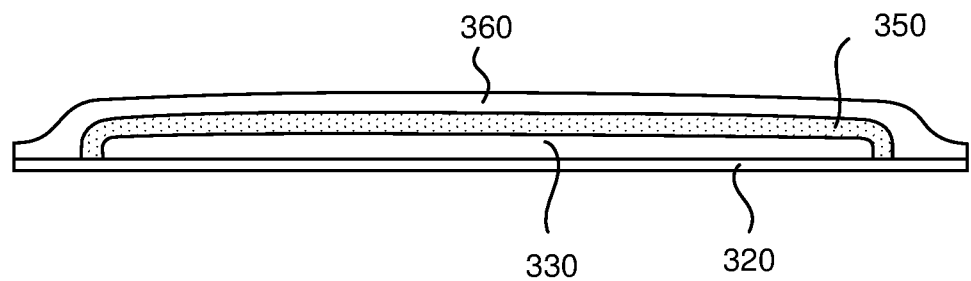
FIG. 2 is a diagrammatic cross sectional view of the conventional defibrillator electrode pad of FIG. 1.
Figure 3:
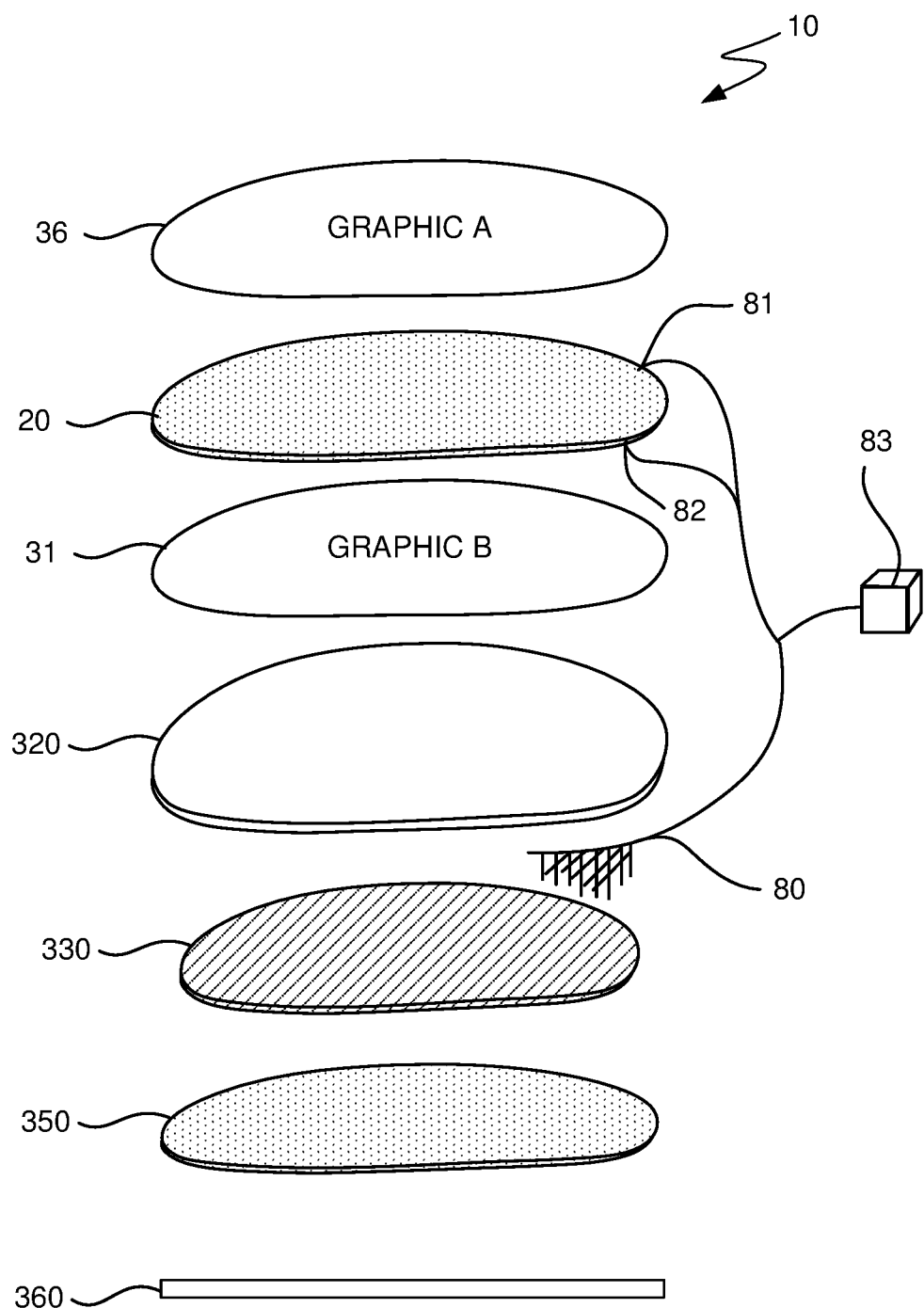
FIG. 3 is a diagrammatic exploded perspective view of a defibrillator electrode pad in accordance with an embodiment of the invention.
Figure 4:
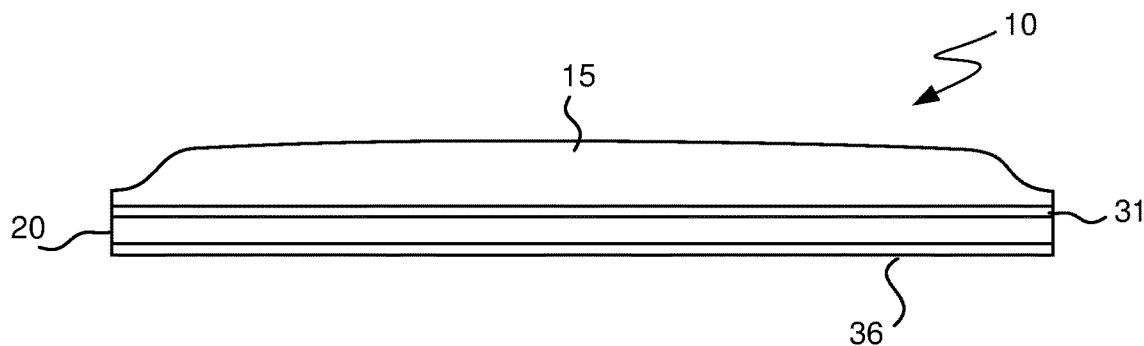
FIG. 4 is a diagrammatic cross sectional view of the electrode pad of FIG. 3.

A particular laminate, graphically active electrode pad construction is illustrated in FIG. 3. The illustrated embodiment, the graphically active defibrillation electrode pad 10 includes a base electrode pad structure 15 having an electrochromic layer 20 laminated thereon. For the purpose of this description, the base pad structure 15 can take a wide variety of different forms and generally has the constituents of a traditional defibrillation electrode pad. This may include layers such as those discussed above with respect to FIGS. 1 and 2 or a wide variety of other suitable forms. Typically, the back of base pad structure 15 is an outer insulating layer. In the illustrated embodiment, the base pad structure 15 includes a back layer 320, a conductor layer 330, a conductive gel layer 350 and a removable release carrier sheet 360 which is sometimes referred to as a release layer.

Graphics or graphics layers (30, 35) are provided on either side of the EC layer 20. In some embodiments, the inner (lower) graphic 30 is simply printed on the back surface of the base pad structure 15. That is, on the outer surface of the outer insulating layer of the base electrode pad structure. Similarly, the outer (upper) graphic 35 may simply be printed on the outer surface of the EC layer 20. In other embodiments, the graphics may be printed on associated substrates (e.g., thin film layers 31, 36) that are located between or on their respective adjacent layers. For example, in some embodiments the inner graphic 30 is part of a lower graphic layer laminated between the base pad structure 15 and the EC layer 20. Similarly the outer graphic 35 may be part of an upper graphic layer 36 that is laminated over the outer surface of EC layer 20. In the following discussion, unless the specific context suggests otherwise, the terms graphics and graphic layers are used interchangeably to refer to the graphics themselves and any associated dedicated substrate that the graphics may be applied to. As such, it should be understood that a graphic printed on another component may sometimes be referred to as a graphic layer and the term graphic layer should not be construed as requiring, but may optionally include, a separate dedicated substrate for the graphic.

When the EC layer 20 is not activated it is opaque. In this state, a user will only see the outermost exposed graphic (35). When the EC layer is activated it becomes transparent and clear, so the user will now also see the inner graphic layer (31) in addition to the outermost layer (36), with the outer graphic 35 being superimposed over the inner graphic 30.

Figure 10:
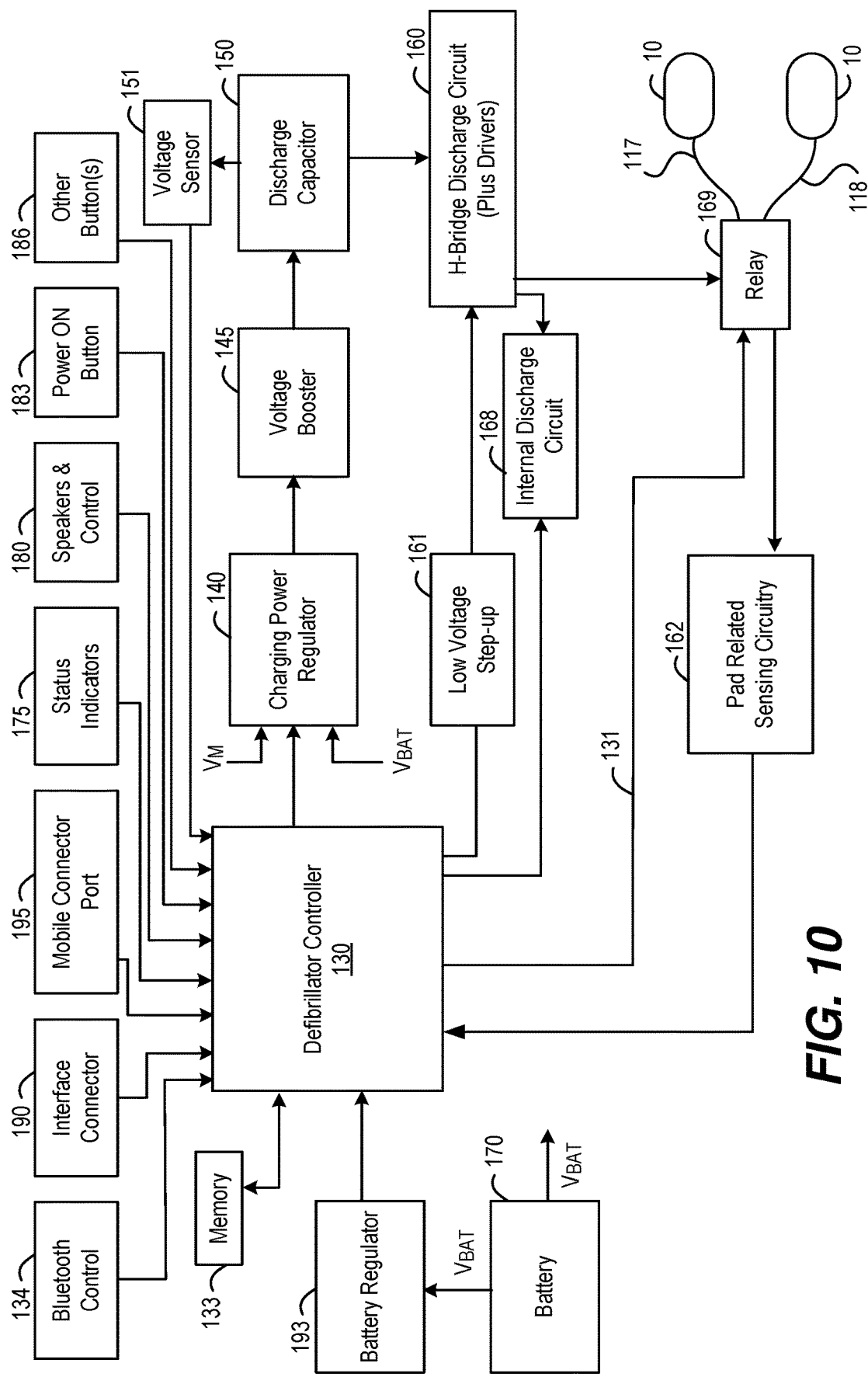
FIG. 10 is a diagrammatic illustrate of defibrillator control electronics suitable for controlling graphically responsive defibrillation electrode pads.

Each defibrillation electrode pad 10 has three associated leads 80, 81 and 82. Electrode lead 80 is coupled to the conductor layer of the base pad structure 15 for delivering the defibrillation shock from a connected AED to the electrode pad and for transmitting sensed ECG signals from the electrode pad 10 to the AED. Leads 81, 82 are control leads for the EC layer 20. The opposing ends of lead 80-82 terminate at a pad assembly connector 83 designed to plug into a mating connector on a defibrillator, such as an AED. The defibrillator has electronic circuitry for sensing ECG signals detected by a pair of defibrillation electrode pads and for delivering defibrillation shock via the electrode pads. The defibrillator connector also has one or more control lines 131 controlled by a defibrillator controller 130 (as best seen in FIG. 10) that connect to control leads 81 and 82. Thus, the defibrillator controller can control the state of the EC layer, and therefore the images visible to a user, via control leads 81 and 82. In some alternative embodiments, the electrode lead 80 can also serve as one of the control leads 81 or 82.

The EC layer is activated by applying an appropriate voltage thereto which creates drop across the EC layer. The defibrillator controller 130 controls the state of the EC layer via control leads (81, 82) control line(s) 131 and control leads 81, 82. The activation & state change within the EC layer is essentially instantaneous from the time that the voltage is applied or removed from the EC layer. As such, the graphics state also changes essentially instantaneously and can readily be controlled by the defibrillator controller.

Figure 5:
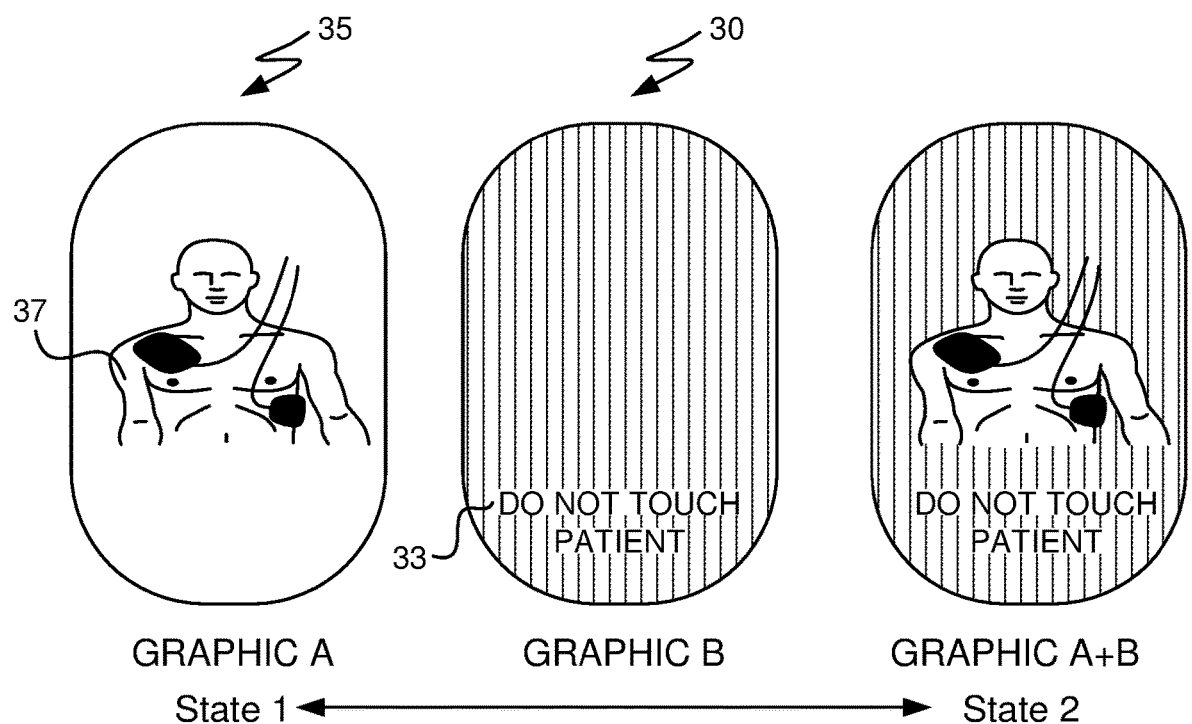
FIG. 5 illustrates two representative graphic layers and the resulting image when the two graphic layers are combined.

FIG. 5 illustrates one manner in which a defibrillation electrode pad's displayed graphics may be controlled using a single EC layer pad structure such as the arrangement shown in FIG. 3. In the illustrated embodiment, Graphic A is an image 37 showing proper defibrillator pad placement on the chest of a patient. Graphic B is a textual warning "DO NOT TOUCH PATIENT" 33 positioned on a red background. Graphic A is used as the outer graphic 35 and Graphic B is used as the inner graphic 30. When the EC layer 20 is not activated (State 1) it is opaque and a user will only see Graphic A over the opaque background of the EC layer as seen on the left side of FIG. 5. In contrast, when the EC layer 20 is activated (State 2), the EC layer becomes transparent so that the user sees a composite of Graphic A superimposed over Graphic B as seen on the right side of FIG. 5. The resulting composite image is a warning with a red background and the highlighted text "DO NOT TOUCH PATIENT" while still showing the desired placement of the defibrillation electrode pads. In this embodiment, the images of Graphics A&B have effectively been added together to create the resulting composite image. The color of the background changes from white (or other opaque color the EC layer has) to red which is likely to be noticed immediately by a responder giving CPR (or otherwise working with the patient).

When this type of "do not touch the patient" type instruction is used, the change from State 1 to State 2 is preferably synchronized with audio (and/or visual) instructions provided by the defibrillator instructing the responder not to touch and/or move away from the patient. Thus, the highly noticeable change in the color of the defibrillation electrode pads and the accompanying text, helping more effectively convey the message of the accompanying audio and/or visual instruction provided by the defibrillator.

Figure 6:
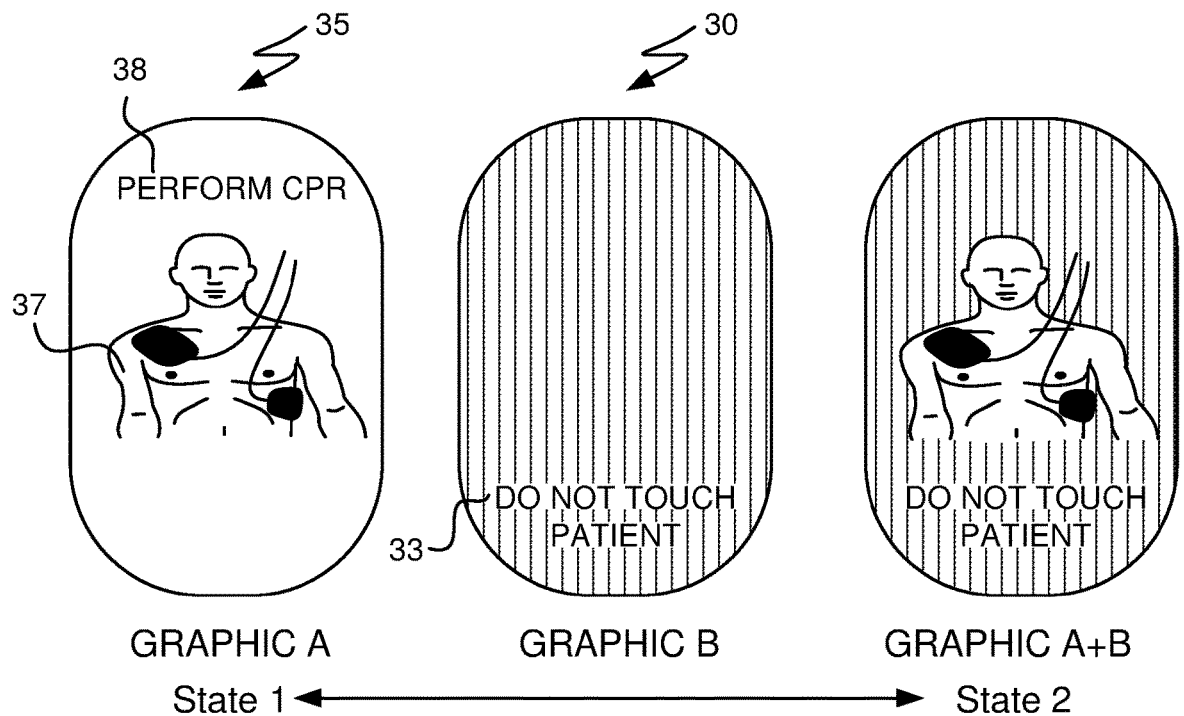
FIG. 6 illustrates two other representative graphic layers and the resulting image when the two graphic layers are combined, with the combined image having a subtractive component.

FIG. 6 illustrates another manner in which the defibrillation electrode pad's displayed graphics may be controlled using a single EC layer pad structure. In this embodiment, both additive and subtractive aspects are used. In this embodiment, Graphic A again includes an image 37 showing proper defibrillator pad placement on the chest of a patient. Graphic A also includes red text 38 instructing the responder to perform CPR on the patient. Graphic B is the same as in the example of FIG. 5 and includes the textual warning "DO NOT TOUCH PATIENT" 33 positioned on the red background. Graphic A is used as the outer graphic 35 and Graphic B is used as the inner graphic 30. When the EC layer 20 is not activated (State 1) it is opaque and a user will only see Graphic A which includes the instruction to PERFORM CPR over the opaque background of the EC layer as seen on the left side of FIG. 6. In contrast, when the EC layer 20 is activated (State 2), the EC layer becomes transparent so that the user sees a composite of Graphic A superimposed over Graphic B as seen on the right side of FIG. 6. The resulting composite image is a warning with a red background and the highlighted text "DO NOT TOUCH PATIENT" while still showing the desired placement of the defibrillation electrode pads. In this embodiment, the composite of Graphics A&B seen in State 2 causes the red lettering "PERFORM CPR" from Graphic A to effectively disappear into the red background from Graphic B such that the "PERFORM CPR" instruction cannot be seen. Thus, the composite of Graphics A&B generated by activating the EC layer 20 effectively subtracts part of the image seen in State 1 (i.e., the PERFORM CPR instruction) while adding a different instruction (DO NOT TOUCH PATIENT) and the red background.

Figure 7:
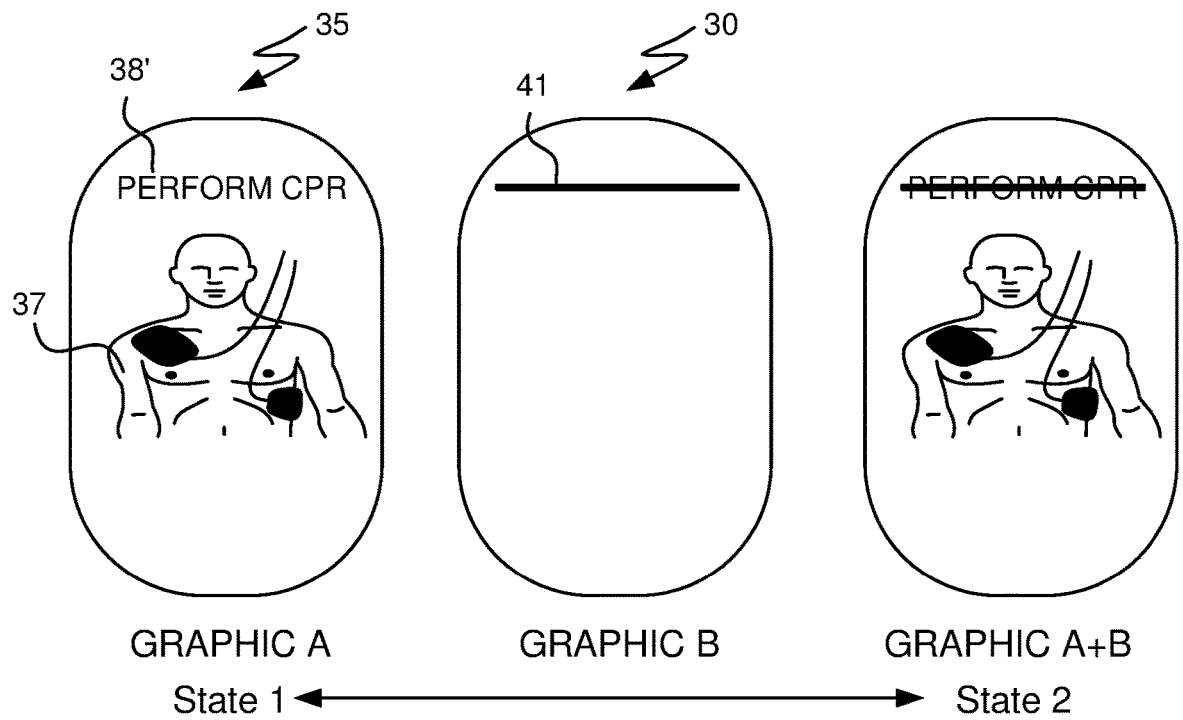
FIG. 7 illustrates two additional representative graphic layers and the resulting image when the two graphic layers are combined that illustrates the use of a strikethrough feature.

FIG. 7 shows yet another combination of graphic images that can be accomplished using a single EC layer 20. In this embodiment Graphic A includes the "PERFORM CPR" instruction 38' and Graphic B includes a block out element 41 having the same color as instruction 38'. As can be seen on the right side of FIG. 7, this approach can be used to effectively hide, or strike through portions of the graphics shown on the outer graphic 35.

Figure 8A:
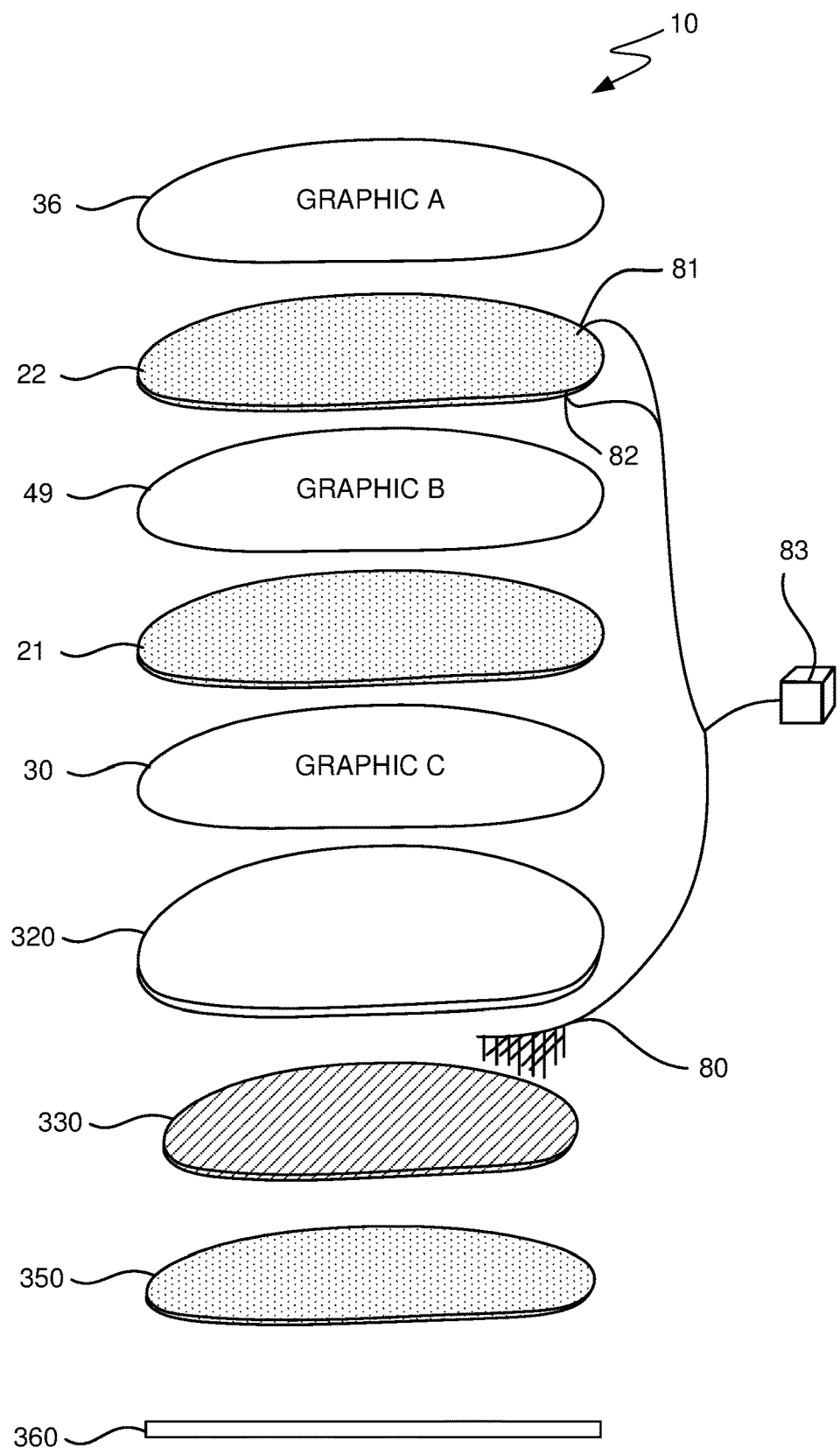
FIG. 8(a) is a diagrammatic exploded perspective view of a defibrillator electrode pad that includes three graphic layers.
Figure 8B:
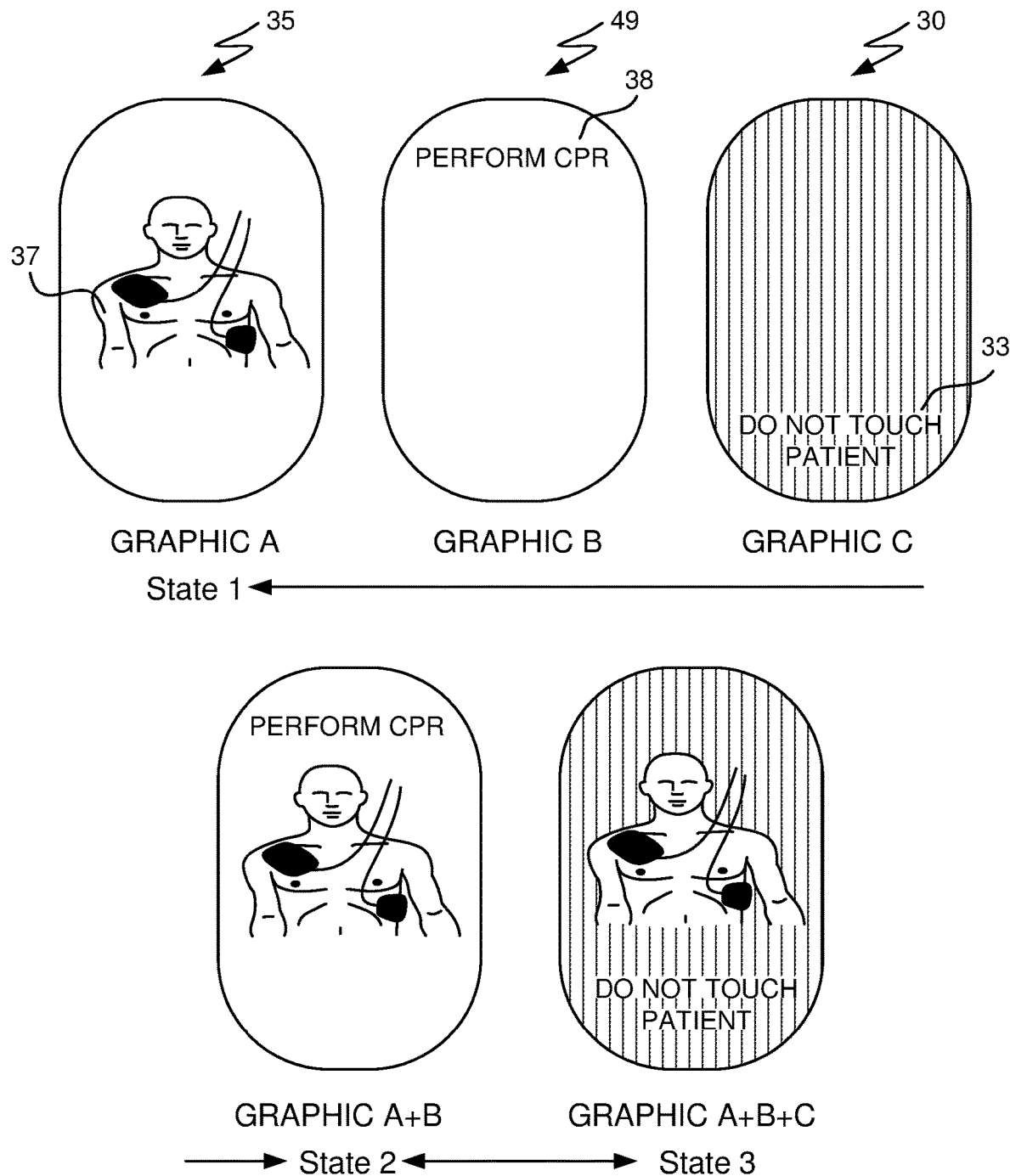
FIG. 8(b) illustrates three representative graphic layers and the resulting combined images in different presentation states.

The same concepts can be used with multiple EC layers to provide even more variability in the messages conveyed by the defibrillation electrode pads 10. FIGS. 8(*a*) and 8(*b*) illustrate a defibrillation pad electrode having three graphics A, B & C and two EC layers.

Graphic A again includes an image 37 showing proper defibrillator pad placement on the chest of a patient. Graphic B includes red text 38 instructing the responder to perform CPR on the patient. Graphic C is the same as Graphic B in the example of FIG. 5 and includes the textual warning "DO NOT TOUCH PATIENT" 33 positioned on a red background. Graphic A is used as the outer graphic 35, Graphic C is used as the inner graphic 30 and Graphic B is an intermediate graphic 49.

With this structure, three different display states are possible. When neither EC layers 21 nor 22 are activated (and are therefore opaque), only Graphic A is seen as represented by State 1. In the illustrated embodiment, this displays only the image 37 showing proper pad placement. When outer EC layer 22 is activated, then Graphics A & B can be seen. In the illustrated embodiment, this causes the pad to display the instruction "PERFORM CPR" 38 in red lettering above the image 37 showing proper pad placement as represented by State 2.

When both the inner EC layer 21 and the outer EC layer 22 are activated, graphics A, B and C are all combined. In the illustrated embodiment, this results in the display represented by State 3. The red lettering of PERFORM CPR instruction 38 effectively disappears into the red background of Graphic C. At the same time, DO NOT TOUCH PATIENT instruction 33 of Graphic C becomes visible below the image 37.

Although only a few examples are provided, it should be apparent that the described approach can be used to display a wide variety of different images, messages, warnings, and instructions during use of a defibrillator.

Masking of the lower layers may be accomplished using any suitable controllable layers, including the described electrochromic layers. The controllable layers may be stacked in series of two, three or more independently controllable layers as described in the embodiments discussed above. In other embodiments a single layer may have multiple independently controllable segments so that selected portions of the graphics on the lower levels can be independently revealed or hidden. Stated another way, EC layer segments can be provided in parallel such that they cover only a portion of the graphical area, are applied on the same plane, and are not overlapping. In this way, different specific areas of the electrode pad surface can become divergent graphical displays & effectively different graphic display pathways. For example, one area of the electrode can be EC activated, while the other is not, allowing for two different graphical pathways & displays. Half 1 can be in state 2, while Half 2 is in state 1, etc. Such segmentation can significantly increase the number of possible graphical states.

In some of the embodiments described above, the electrochromic (or other controllable) layers are opaque in the inactive state and are transparent and clear in the activated state. In other embodiments, the electrochromic layers can be colored to effectively provide a different colored background when activated. For example, a red background can be provided by utilizing an electrochromic material that turns red when activated, or a green background can be provided by utilizing an electrochromic material that turns green when activated. In other embodiments, the controllable layer may be transparent and colored when activated, which allows graphics behind the EC layer to be seen in addition to changing the background color.

Figure 9:
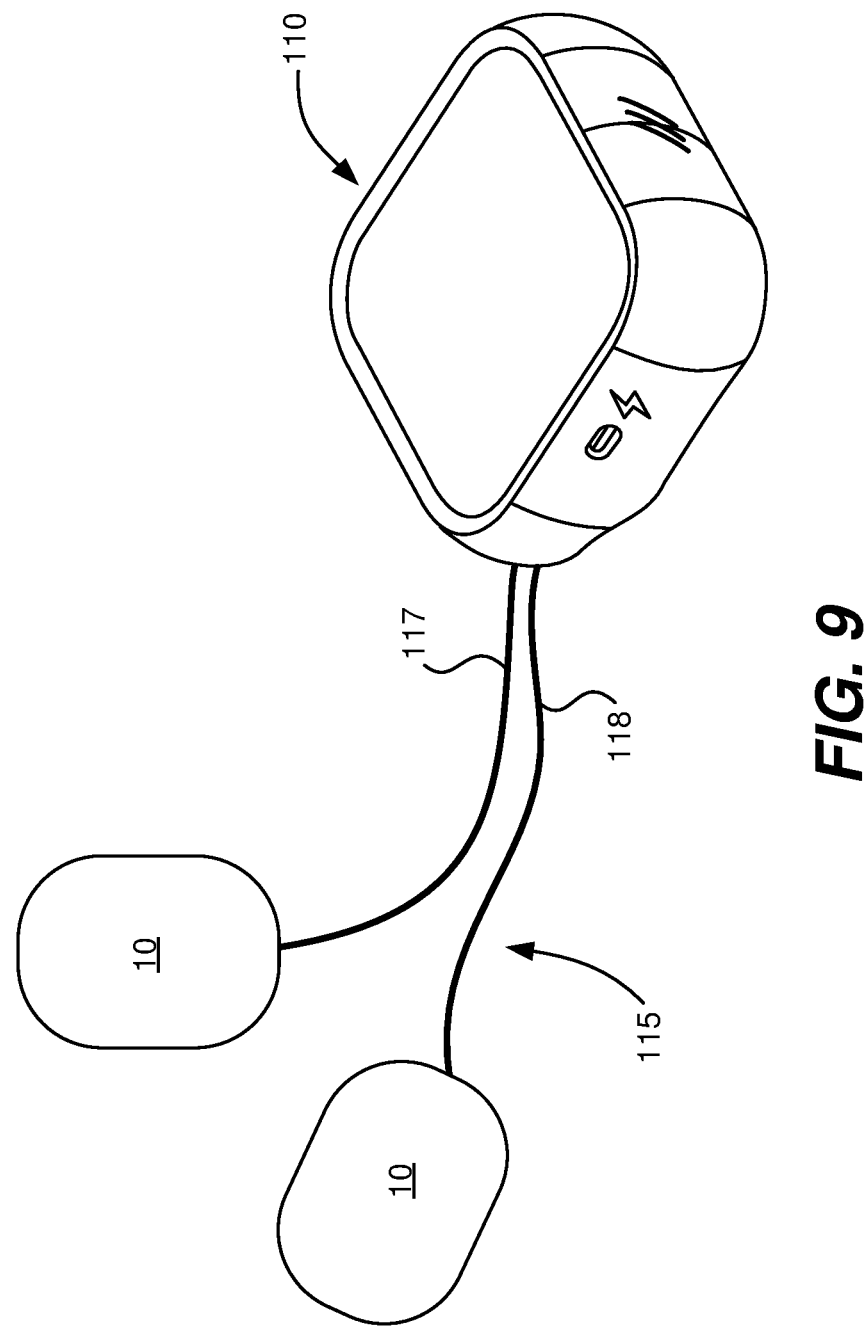
FIG. 9 is a diagrammatic illustration of a defibrillator system having a base defibrillation unit and a pad assembly that includes a pair of graphically responsive defibrillation electrode pads.

FIG. 9 is a diagrammatic illustration of a defibrillator system that includes an automated external defibrillator unit 110 and an electrode pad assembly 115 that includes a pair of defibrillation electrode pads 10 and a pad assembly connector. The pad assembly connector cannot be seen in FIG. 9 since it is connected internally within the defibrillation unit 110. Cables 117 and 118 couple the electrode pads 10 to the connector. Each cable includes three associated leads 80, 81, and 82 as discussed previously.

FIG. 10 is a block diagram illustrating one representative electronics control architecture and associated components suitable for use in the defibrillator unit 110 that controls the state of the described graphically active defibrillation electrode pads. The illustrated architecture is well suited for use in automated external defibrillators (including both semi-automated and fully automated defibrillators) although it may also be used in manual defibrillators and hybrid defibrillators that may be used in either automated or manual modes. In the illustrated embodiment, the electronic components include a defibrillator controller 130, memory 133, a wireless communications module in the form of a wireless communications module in the form of short range communications (e.g., Bluetooth®) module 134, a charging power regulator 140, a voltage booster 145 (which may have multiple stages), a high voltage capacitor 150 for temporarily storing sufficient electrical energy suitable to provide a defibrillation shock, shock discharge control circuitry 160, internal discharge circuitry 168, pad related sensing circuitry 162 and relays 169, power storage unit 170, battery regulator 193, status indicator(s) 175, speaker(s) 180 and one or more electrical connectors (e.g., interface connector 190, mobile connector port 195, charger connector (not shown), etc). The charging power regulator 140 and voltage booster 145 which cooperate to control the charging of the shock discharge capacitor 150 are sometimes referred to herein as a charging circuit.

The defibrillator controller 130 is configured to control the operation of the base defibrillator unit and to direct communications with external devices, as appropriate. In some embodiments, the defibrillator controller includes one or more processors arranged to execute software or firmware having programmed instructions for controlling the operation of the base unit, directing interactions with a user and communications with external components. More details of the defibrillator electronics are described in U.S. Patent application Ser. No. 62/871,915 and Ser. No. 16/145,657, each of which is incorporated herein by reference.

The relays 169 are configured to switch between an ECG detection mode in which the patient electrode pads 10 are coupled to the pad related sensing circuitry 162 via electrode lead 80, and a shock delivery mode in which the patient electrode pads 116 are connected to discharge circuitry 160 via electrode lead 80 to facilitate delivery of a defibrillation shock to the patient. The pad related sensing circuitry 162 may include a variety of different functions. By way of example, this may optionally include a pad connection sensor, ECG sensing/filtering circuitry, and impedance measurement filter.

The relays 169 also decouple the EC layer control leads 81, 82 from defibrillator controller 130 when the relays are in the shock delivery mode. Although specific components are described, it should be appreciated that their respective functionalities may be provided by a variety of other circuits.

The base defibrillator unit also includes a number of software or firmware control algorithms installed in memory 133 and executable on the defibrillator controller 130. The control algorithms have programmed instructions suitable for controlling operation of the base unit and for coordinating the described broadcasts, as well as any point-to-point communications between the base unit 110 and any connected interface devices. These control routines include (but are not limited to): communication control algorithms, heart rhythm classification algorithms suitable for identifying shockable rhythms; capacitor charge management algorithms for managing the charging of the discharge capacitor; capacitor discharge management algorithms for managing the delivery of a shock as necessary; user interface management algorithms for managing the user instructions given by the defibrillator and for controlling the state of the EC layer(s) in the defibrillation electrode pad to provide appropriate instructions during an emergency; battery charge control algorithms for managing the charging of power storage unit 170; testing and reporting algorithms for managing and reporting self-testing of the base unit; software update control algorithms and verification files that facilitate software updates and the verification of the same.

In some embodiments, a single processor is used as defibrillator controller 130. In other embodiments, multiple processors may be used. For example, the defibrillator controller 130 may include a master processor and a slave processor, with the slave processor being solely responsible for managing the charging and discharging of the discharge capacitor 150.

Although only a few embodiments of the invention have been described in detail, it should be appreciated that the invention may be implemented in many other forms without departing from the spirit or scope of the invention. Therefore, the present embodiments should be considered illustrative and not restrictive and the invention is not to be limited to the details given herein, but may be modified within the scope and equivalents of the appended claims.

What is claimed is:

1. A defibrillation electrode pad comprising:
an insulating layer;
a conductive layer positioned on a first side of the insulating layer;
a conductive gel in electrical contact with the conductive layer on the first side of the insulating layer, the conductive gel layer being configured to be placed into contact with skin of a patient to facilitate delivery of a defibrillation shock through the conductive gel;
a first graphic printed on or positioned over a second side of the insulating layer;
a second graphic, the second graphic being visible on a back side of the defibrillation electrode pad; and
an electrochromic layer located between the first and second graphics, the electrochromic layer being configured such that a current state of the defibrillation electrode pad can be controllably switched back and forth between first and second states during emergency use of the graphically responsive defibrillation electrode pad with the defibrillation electrode pad adhered to a patient suitably for delivering a defibrillation shock via the conductive layer and conductive gel, the electrochromic layer being configured to hide the second graphic when the electrochromic layer is in the first state and to render the second graphic visible when the electrochromic layer is in the second state to thereby cause a composite image that combines the first and second graphics to be visible on the back side of the defibrillation electrode pad, whereby the electrochromic layer is electrically isolated from the conductive layer and the conductive gel by the insulating layer.

2. The defibrillation electrode pad as recited in claim 1 wherein:
the first graphic is printed on the second side of the insulating layer; and
the second graphic is printed on the electrochromic layer.

3. The defibrillation electrode pad as recited in claim 1 wherein:
the first graphic is part of a first graphic layer positioned between the insulting layer and the electrochromic layer; and
the second graphic is part of a second graphic layer positioned on an opposite side of the electrochromic layer relative to the first graphic layer.

4. The defibrillation electrode pad as recited in claim 1 wherein the electrochromic layer is substantially opaque in the first state and substantially transparent in the second state such that the second graphic is hidden when the electrochromic layer is in the first state and visible when the electrochromic layer is in the second state.

5. The defibrillation electrode pad as recited in claim 1 further comprising a third graphic and a second electrochromic layer, wherein:
the third graphic is printed on or positioned over the second side of the insulting layer;
the second electrochromic layer is positioned between the third and first graphics; and
the second electrochromic layer is configured to hide the third graphic when the second electrochromic layer is in an opaque state and to render the third graphic visible when the second electrochromic layer is in a transparent state and the first graphic is visible to thereby cause a composite image that combines the first, second, and third graphics to be visible on the back side of the defibrillation electrode pad.

6. The defibrillation electrode pad as recited in claim 1 wherein the electrochromic layer is:
opaque in the first state; and
transparent and clear in the second state.

7. The defibrillation electrode pad as recited in claim 1 wherein the electrochromic layer is:
opaque in the first state; and
transparent and colored in the second state such that a color of the back of the defibrillation electrode pad changes when the electrochromic layer transitions from the first state to the second state.

8. A defibrillator pad assembly comprising the defibrillation electrode pad as recited in claim 1 and a cable, the cable including:
a defibrillation lead electrically coupled to the conductive layer and configured to facilitate delivering a defibrillation shock from a defibrillator to a patient via the defibrillation electrode pad when the cable is connected to the defibrillator and the defibrillation electrode pad is attached to the patient; and
at least one control lead coupled to the electrochromic layer to facilitate control of the electrochromic layer.

9. The defibrillation electrode pad as recited in 1 wherein the electrochromic layer defaults to the first state when no power is applied to the electrochromic layer.

10. The defibrillator pad assembly comprising a pair of defibrillation electrode pads as recited in claim 1, the defibrillator pad assembly further comprising:
a connector suitable for electrically connecting the defibrillator pad assembly to a defibrillator;
a first cable for electrically coupling a first one of the pair of defibrillation electrode pads to the connector; and
a second cable for electrically coupling a second one of the pair of defibrillation electrode pads to the connector.

11. A defibrillator system comprising the defibrillator pad assembly as recited in claim 10, the defibrillator system further comprising:
a base defibrillator unit including a defibrillator controller and defibrillation shock delivery circuitry.

12. The defibrillator system as recited in claim 11 wherein the defibrillator controller is configured to control the states of the electrochromic layers in the pair of defibrillation electrode pads.

13. A defibrillation electrode pad comprising:
a base electrode pad structure suitable for delivering a defibrillation shock to a patient, the base electrode pad including an insulating layer and a conductive gel layer positioned over a front side of the insulating layer, the conductive gel layer being configured to be placed into contact with skin of the patient to facilitate delivery of the defibrillation shock through the conductive gel;
a first graphic printed on, or positioned over a back side of the insulating layer;
a second graphic, the second graphic being visible on a back side of the defibrillation electrode pad; and
a controllable layer positioned between the first graphic and the second graphic and configured to hide the first graphic when the controllable layer is in a first state and to render the first graphic visible when the controllable layer is in a second state to thereby cause a composite image that combines the first and second graphics to be visible on the back side of the defibrillation electrode pad, whereby the controllable layer is electrically isolated from the conductive gel by at least the insulating layer.

14. A defibrillator pad assembly comprising a pair of defibrillation electrode pads as recited in claim 13, the defibrillator pad assembly further comprising:
- a connector suitable for electrically connecting the defibrillator pad assembly to a defibrillator;
- a first cable for electrically coupling an associated first one of the pair of defibrillation electrode pads to the connector; and
- a second cable for electrically coupling an associated second one of the pair of defibrillation electrode pads to the connector; and
- wherein the first and second cables each include,
    - (i) a defibrillation lead electrically coupled to the base electrode pad structure of the associated one of the defibrillation electrode pads, and
    - (ii) at least one control lead coupled to the controllable layer of the associated defibrillation electrode pad to facilitate control of the controllable layer of the associated defibrillation electrode pad.

15. A graphically responsive defibrillation electrode pad arranged to selectively display different images during use of the graphically responsive defibrillation electrode pad, wherein:
- in a first state, a first image is visible on a back side of the graphically responsive defibrillation electrode pad and in a second state a second image is visible on the back side of the graphically responsive defibrillation electrode pad, the second image being at least partially different than the first image; and
- the graphically responsive defibrillation electrode pad is configured such that a current state of the graphically responsive defibrillation electrode pad can be controllably switched back and forth between the first and second states during emergency use of the graphically responsive defibrillation electrode pad with the graphically responsive defibrillation electrode pad adhered to a patient suitably for delivering a defibrillation shock through the graphically responsive defibrillation electrode pad.

16. A defibrillator pad assembly comprising a pair of graphically responsive defibrillation electrode pads as recited in claim 15, the defibrillator pad assembly further comprising:
- a connector suitable for electrically connecting the defibrillator pad assembly to a defibrillator;
- a first cable for electrically coupling a first one of the pair of graphically responsive defibrillation electrode pads to the connector; and
- a second cable for electrically coupling a second one of the pair of graphically responsive defibrillation electrode pads to the connector.

17. The defibrillator system comprising a defibrillator pad assembly as recited in claim 16, the defibrillator system further comprising:
- a base defibrillator unit including a defibrillator controller and defibrillation shock delivery circuitry; and
- wherein the defibrillator controller is configured to control the images displayed by the graphically responsive defibrillation electrode pads during emergency use of the defibrillator system.

* * * * *